United States Patent [19]

Miller et al.

[11] 4,133,874

[45] Jan. 9, 1979

[54] LIPID ENCAPSULATED HEMOGLOBIN CELLS

[75] Inventors: Irving F. Miller, Evanston; Ljubomir Djordjevich, Chicago, both of Ill.

[73] Assignee: The University of Illinois Foundation, Urbana, Ill.

[21] Appl. No.: 876,717

[22] Filed: Feb. 10, 1978

Related U.S. Application Data

[63] Continuation-in-part of Ser. No. 694,903, Jun. 10, 1976.

[51] Int. Cl.$^2$ .................. A61K 9/42; A61K 9/50; A61K 35/14; A61K 35/18
[52] U.S. Cl. ............................ 424/38; 252/316; 424/101; 424/365
[58] Field of Search ............ 424/3, 34, 35, 36, 37, 424/38, 101, 365; 252/316; 195/1.7, 1.8

[56] References Cited

U.S. PATENT DOCUMENTS

3,887,698  6/1975  McConnell .................. 424/13 X

FOREIGN PATENT DOCUMENTS

2236909  2/1974  Fed. Rep. of Germany ............ 424/78

OTHER PUBLICATIONS

Koszo, Biochem. & Biophys, Acta, vol. 363, 1974, pp. 182–189.
Papahadjopoulos, Biochem. & Biophys. Acta, vol. 363, 1974, pp. 408–418.
Nicholls, Biochem. & Biophys. Acta, vol. 363, 1974, pp. 190–201.
Merck Index, Merck & Co., Rahway, N.J., 7th Ed., 1960, pp. 245, 509.
Gregoriadis, Febs Letters, vol. 36, No. 3, Nov. 1973, pp. 292–296.
Calissano, Biochem. & Biophys, Res. Comm., vol. 43, 1971, pp. 504–509.
Schubert, Chem. Abs., vol. 79, 1973, Ab. No. 122811s.

*Primary Examiner*—Anna P. Fagelson
*Attorney, Agent, or Firm*—Merriam, Marshall & Bicknell

[57] ABSTRACT

Synthetic erythrocytes. Hemoglobin is encapsulated in lipid materials to form cells which are typically 0.1 to 10 microns in their greatest dimension. Preferably cholesterol and one or more phospholipids are included in the cell membrane. The lipid membrane is of such character and thinness that $O_2$—$CO_2$ transfer thereacross is readily accomplished. The preferred encapsulation process utilizes ultrasonic energy.

10 Claims, No Drawings

LIPID ENCAPSULATED HEMOGLOBIN CELLS

CROSS-REFERENCE TO RELATED APPLICATION

This is a continuation-in-part of our co-pending application Ser. No. 694,903, filed June 10, 1976.

BACKGROUND OF THE DISCLOSURE

Our invention relates to cells consisting of hemoglobin encapsulated in lipids and more especially phospholipids and to the method of making such synthetic cells. These cells are characterized by comparable $O_2$—$CO_2$ conjugation and transference to that of naturally occurring red blood cells. Furthermore, our synthetic cells are of such small size and flexibility to readily pass through mammalian capillary systems where such $O_2$—$CO_2$ transfer takes place. Another, most desirable feature of our cells is that their use introduces no foreign matter to the recipient.

Our synthetic cells, in terms of oxygen carrying capability, function very similarly to normal mammalian red blood cells and accordingly in suspension offer substantial utility as a transfusion liquid. Such cells appear as acceptable to the mammalian host as are natural such cells, function in substantially the same manner and should be metabolized and excreted as are naturally occurring cells.

As is known to those skilled in this art, hemoglobin is a conjugated protein having a prosthetic group — heme — affixed to the protein, globin. It is the red coloring matter of blood and is found, contained, in the red blood cells. Its essential utility stems from its ability to unite in loose combination with atmospheric oxygen to form oxyhemoglobin. In mammals this occurs in the capillaries adjacent the lung alveoli to produce so-called oxygenated blood. This is carried in the arterial system to the tissues where a portion of the oxygen is released and then the venous blood, partially depleted in oxygen, is returned to the lungs for further oxygenation.

As further background we note that heme is an iron porphyrin, i.e., the union of iron with four pyrrole groups. The iron is basically in the ferrous state. Hemoglobin is usually designated as

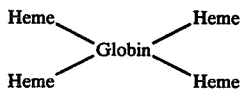

Thus hemoglobin is a tetramer consisting of four sub-units; each sub-unit is a combination of a polypeptide chain, which is the protein or globin part of hemoglobin, and a heme. The latter is the functional unit or active site to which oxygen may be bound.

Whole blood, especially human, when drawn for transfusion purposes, is considered to have a storage life of 21 days. By present regulation, such blood 21 days old must be discarded and no longer used for blood transfusion. As a practical matter upon the passage of such time, the red cells break down thus making the old blood substantially useless for its intended purpose. However, such "old blood" still contains useful, functional hemoglobin and can be used as the starting material in the preparation of the present cells.

In distinction to the aging problem — 21 days — encountered with whole, natural blood, we find that the present cells when appropriately buffered, have quite an extended, useful, shelf life, as is noted below.

Our synthetic hemoglobin cells offer another advantage — because of how they are made they can be considered to be in the class of universal donor. Whole blood for transfusion purposes must be typed and extreme care taken to assure compatability with the blood type of the recipient. This is not the case with the present cells. Our starting material for encapsulation is what is commonly referred to as "stroma-free" hemoglobin. This is hemoglobin free of the cell membranes or membrane fragments of the red blood cells but having associated therewith the normal cell components, such as diphosphoglycerate and carbonic anhydrase, required for $O_2$—$CO_2$ exchange. The membranes of natural erythrocytes contain many different proteins and it is such protein which necessitates blood-typing. The membranes of our synthetic cells are essentially formed of universally present (i.e., in the mammal) lipids and the like which are not subject to antigenic reactions of proteins.

As further background to our invention, we note that the separation of red blood cells from whole blood is an old, established common practice. And the separation of hemoglobin from its associated red cells by a multitude of techniques is similarly well-known. Such two known categories of techniques represent the starting points in forming the hemoglobin cells of this invention.

As further background we also note that some workers have been investigating the use of cell-free hemoglobin solutions as natural blood substitutes. These solutions suffer the disadvantage of being rapidly excreted by the body and thus really do not accomplish their intended purpose for anything but the shortest of times. In distinction to this the present lipid encapsulated hemoglobin cells will be retained by the body for extended and more useful periods.

We also note that prior workers have formed what are generically referred to as liposomes.

Among the prior patents we note the following:

Bower, U.S. Pat. No. 2,527,210 is directed to a hemoglobin solution wherein a freezing-thawing technique is used to destroy the red cell membranes.

Childs, U.S. Pat. No. 3,133,881 discloses a centrifugation method which may be employed to separate red cells from the other constituents of whole blood.

Van Dyck et al., U.S. Pat. No. 3,351,432 is directed to the washing and reconstituting of red blood cells and Ushakoff, U.S. Pat. No. 3,418,209 to making red cells storable by a combination with a glycerin solution. Similarly, Ilg, U.S. Pat. No. Re. 27,359 is directed to the washing of red cells.

Bonhard, U.S. Pat. No. 3,864,478 discloses another method of making a hemoglobin solution.

The prior art teachings in no way suggest or hint at the lipid encapsulation of hemoglobin to form the present synthetic cells nor the benefit or utility of such cells. The similarity of the present synthetic cells to normal red blood cells in terms of oxygen carrying capability is unexpected.

Accordingly, a principal object of our invention is to provide lipid encapsulated hemoglobin — synthetic erythrocytes — and a method for their manufacture. How this is accomplished is set out as this description proceeds.

DETAILED DESCRIPTION

In practicing our invention, hemoglobin is first separated from its associated red blood cell membranes. The basis starting material herein as noted above, is stroma-free hemoglobin; this is the material which we subsequently encapsulate in lipid. We can start with relatively freshly drawn blood which contains a vast majority of viable red blood cells through blood drawn, e.g., 21 days previously or more, wherein a substantial proportion of the red cells no longer are viable. It is important to thoroughly separate the hemoglobin from its natural cell membranes to eliminate the above-noted protein reactions and other adverse reactions in the recipient.

There are numerous known procedures for separating hemoglobin from blood. First the red cells are separated from the plasma constituent by centrifugation or the like. The residue consists of both broken and unbroken red blood cells. By freeze-thawing or controlled osmotic lysis we rupture the remaining cell membranes, although other techniques may be employed, and then by filtration or the like we produce stroma-free hemoglobin solution. Care should be taken to avoid bacterial contamination and small quantities of suitable antibiotic or bacteriostatic agents such as gentamycin and tetracycline or the like may be added to the stroma-free hemoglobin. The concentration of hemoglobin and other constituents may be adjusted as desired.

The resulting hemoglobin solution is then encapsulated in naturally occurring lipids to form synthetic liposome cells. Such cells are typically 0.1 to 10 microns in their largest dimension. We believe that the lipid membrane is approximately two molecules thick.

In the present specification and claims the term "liposome" is used. By this is meant a capsule wherein the wall or membrane thereof is formed of lipids, especially phospholipid, with the optional addition therewith of a sterol, especially cholesterol.

In the preferred method hereof a thin lipid film is first formed on the interior surface of a container. In the laboratory such container is usually a flask of the round bottom type. A small amount of lipid in an organic solvent is placed in the flask and it is both shaken and spun to deposit a thin lipid film on the interior surface. Such film is permitted to dry. Then a small amount of the stroma-free hemoglobin solution is deposited in the flask. While other encapsulation techniques may be employed we prefer the following:

The flask is placed in a water bath maintained at 37° C. and the bath subjected to ultrasound at a frequency of 50,000 Hertz. In the presence of the hemoglobin solution and as a result of such mixing, the lipid material forms a continuous membrane about the hemoglobin solution and forms the cells of the present invention. The cells are then separated from the extracellular hemoglobin solution and suspended in an appropriate carrier liquid.

The film forming materials useful herein are selected from the group phospholipid generically. Representative of the useful phospholipids are synthetic and naturally-occurring lecithins, cephalins and sphingomyelins. Among such phospholipids the following materials exemplify, but are not exhaustive of the herein useful materials: phosphatidic acid, phosphatidyl serine, phosphatidyl inositol, phosphatidyl choline and phosphatidyl ethanolamine.

In addition to the use of phospholipid alone, we find that the use therewith of a sterol compound such as cholesterol greatly enhances those properties of the cell membrane that are desirable for the present application.

We prefer to use both cholesterol and one or more phospholipids together as the encapsulating material. We have found that a suitable encapsulant is 3 parts (by weight) lecithin to 1 part cholesterol. In the examples presented below this is referred to as the "3:1 material," although a "2:1" mixture of lipids would be expected to be equally suitable.

As to the hemoglobin solution as used herein, we prefer a solution containing ions normally present in plasma. However, other ions may be present. The pH is preferably 7.4 and the solution is preferably isoosmotic with normal plasma.

In order to prepare the encapsulating film, the cholesterol/phospholipid is first dissolved in an inert, highly volatile organic liquid such as chloroform. This is evaporated to leave the film on the flask wall.

Examples of how the present cells are produced are as follows:

EXAMPLE 1

60 mg of the 3:1 material was dissolved in 30 ml of reagent grade chloroform in a 1-liter round bottom flask under sterile conditions. Temperature was 25° C. The material was swirled around the flask walls under vacuum for approximately 15 minutes and a thin, transparent film was formed, coating the bottom two-thirds of the flask. Into such coated flask was then deposited 10 ml of hemoglobin solution containing 16 gram percent of hemoglobin as well as other normal soluble intracellular components of red blood cells. Such solution had a pH of 7.4 and was isoosmotic with normal plasma. The flask was then immersed up to its neck in a water bath maintained at 37° C. and ultrasound at a frequency of 50 KHz was applied through the bath for 15 minutes. There resulted 10 ml of encapsulated hemoglobin dispersion having a particle size spectrum ranging between 0.1 and 10 microns. This dispersion was washed three times with normal saline by centrifugation and decantation to produce the final product.

Any unencapsulated hemoglobin may be utilized in a subsequent encapsulation.

EXAMPLE 2

14.4 mg of cholesterol, 43.2 mg of lecithin ex ovo, and 2.4 mg of phosphatidic acid were dissolved in 25 ml of reagent grade chloroform in a 1-liter round bottom flask under sterile conditions. Temperature was 25° C. The material was swirled around the walls, under vacuum, for approximately 15 minutes and a thin, transparent film was formed, coating the bottom two-thirds of the flask. Into such coated flask was then deposited 10 ml of hemoglobin solution containing 15.7 gm percent hemoglobin (plus other normal soluble intracellular components) in isotonic saline. The rest of the procedure follows Example 1.

EXAMPLE 3

20 mg of cholesterol and 100 mg of lecithin ex ovo were dissolved in 25 ml of reagent grade chloroform in a 1-liter round bottom flask under sterile conditions. The rest of the procedure follows Example 1, with the exception that the hemoglobin solution contained 14.71 gm percent hemoglobin (plus other normal soluble intracellular components) in isotonic saline.

EXAMPLE 4

30 mg of cholesterol, 80 mg of lecithin ex ovo, and 10 mg of phosphatidyl serine were dissolved in 25 ml of reagent grade chloroform in a 1-liter round bottom flask under sterile conditions. The rest of the procedure follows Example 3.

EXAMPLE 5

The procedure follows Example 1, with the exception that the hemoglobin solution contained 22 gm percent hemoglobin (plus other normal soluble intracellular components) in isotonic saline.

The encapsulated hemoglobin cells resulting from Example 1 were tested as follows:

Gas mixtures consisting of varying proportions of oxygen, nitrogen, and carbon dioxide, at one atmosphere total pressure, were equilibrated with samples of the present encapsulated hemoglobin, and the relative oxygen saturation of the hemoglobin was determined by spectrophotometry. The results were as follows:

| $pO_2$ (mm Hg) | $pCO_2$ (mm Hg) | % $O_2$ saturation |
|---|---|---|
| 10 | 44 | 14.9 |
| 20 | 45 | 28.7 |
| 30 | 42 | 46.3 |
| 40 | 42 | 62.3 |
| 50 | 41 | 72.0 |
| 60 | 41 | 85.7 |
| 70 | 40 | 89.5 |
| 90 | 40 | 90.7 |

These results, obtained at 22° C. and a pH of 6.35, closely follow what would be obtained for normal whole blood under the same conditions.

In the practice of the present invention we prefer to use ultrasonic energy as the means for encapsulation. However, other means of providing vigorous stirring of the hemoglobin-lipid-cholesterol may be employed. Intimate mixing of the hemoglobin and cell membrane material is required.

The resulting cell size can be fairly closely controlled, the aim of course being to have cells capable of unhindered capillary passage. Cell size is dependent upon factors such as: temperature, viscosity, stirring frequency, interfacial tension as between membrane material and the aqueous phase hemoglobin being encapsulated, and other physical properties. Lower stirring energy levels than we have used would likely result in reduced cell forming efficiency.

It is interesting to note that cell size in the present invention is substantially self-governing. Cells larger than 10 microns appear somewhat unstable and break down into smaller units. And, of course, liposomes too big for intended use may readily be filtered out.

There is another aspect of the present hemoglobin liposomes that should be noted. Normally occurring red blood cells are characterized by slight surface electronegativity commonly measured in terms of "zeta potential." Under conditions comparable to those used in the oxygenation study described above, red blood cells are characterized by zeta potentials in the range of −8 to −17 millivolts. By controlling the relative proportions of certain cell membrane forming materials hereof (e.g., the electronegative phospholipids such as phosphatidic acid or its functional equivalent, dicetyl phosphate) we can vary the zeta potential measurements of our synthetic cells across this range and in fact have found that cells formed from Example 3 have a zeta potential of −22 millivolts. The various phospholipids used herein are characterized by varying electronegativities. Such electronegativity in both natural and our synthetic erythrocytes is believed to be physiologically significant inter alia to both keep the cells separated from each other in the blood stream and from the blood vessel walls. Further, the tendency toward agglutination of synthetic erythrocytes may be reduced by the addition of small amounts of albumin to the stroma-free hemoglobin prior to encapsulation.

In the present hemoglobin liposomes the cell membrane is preferably a bilayer although multilayers may be used. Within the limit of providing adequate hemoglobin encapsulation, it is preferred that the cell wall be as thin as possible to enhance $O_2$—$CO_2$ exchange.

It will be evident to those skilled in the art associated with the present invention that the present hemoglobin liposomes essentially contain materials naturally occurring in the mammalian host. Such cells may be used for blood transfusion purposes (e.g., in isotonic saline or Krebs-Ringers solutions or in synthetic plasma materials such as dextran or hydroxyethyl starch solutions and the like) with a comparative long life in the body of the host, as compared with free hemoglobin, and also will be naturally metabolized for subsequent excretion. Even more specifically, synthetic erythrocytes of the invention may be stored, "packed," re-constituted and administered according to standardized techniques well known in the art of "banking" and transfusing natural erythrocytes. In this respect, see, e.g., "Blood Banking and the Use of Frozen Blood Products" (CRC Press, Cleveland, Ohio, 1976) pp. 38–39, 107–110, 360–361; "Transfusion of Blood Preserved by Freezing" (Igaku Shoin, Tokyo, 1973) pp. 28–44; and "Quality Control in Blood Banking" (John Wiley & Sons, New York, New York, 1974) pp. 137–144; 197–198.

Furthermore, our cells appear sturdier than normal red blood cells which should prove useful in extracorporeal functions such as in conjunction with heart-lung machines or artificial kidney machines. In addition to this, such synthetic cells are expected to have a reasonably good shelf life beyond the 21 days of whole blood. At a pH of 6.5 we found that after two and six weeks respectively of storage there still remained 50% and 25% of active hemoglobin in our liposomes. At a pH of 7.4 the results would be expected to be better.

The following are examples of in vivo administration of synthetic erythrocytes of the invention which were prepared using a synthetic lecithin (about 13 parts by weight), cholesterol (about 5 parts) and phosphatidic acid (about 2 parts) as the encapsulating material.

EXAMPLE 6

The material administered contained 25% cells by volume (Hct) suspended in 1 liter of Krebs-Ringers solution (pH 7.4). The cells suspended contained 10 gm hemoglobin/100 cc (i.e., 10 gm percent). A total of 8 to 10 cc of solution was administered to a rat in two batches — 4 cc of blood was removed and 4 cc of solution was infused and this process was repeated — effectively replacing about 40% of the animal's blood volume. The animal survived for about 30 minutes and upon attempting to remove an additional 10 cc of blood, the rat was inadvertently killed. Close inspection of tissue evidenced no adverse immunological effects.

EXAMPLE 7

The material administered contained 30–40% by volume of cells, containing 12 gm percent hemoglobin, in Krebs-Ringers solution (pH 7.4) including an antibiotic. The material was administered to 4 rats with the following results.

(a) Poor technique was employed in administering the material to the first rat, and resulted in the animal's death.

(b) The cannula employed to administer the material to a second rat pulled out inadequately and the animal bled to death.

(c) In the third rat, approximately 16 cc of the material — about 100% of the entire blood volume — was exchanged. The animal died of pulmonary edema about 30 minutes after the start of the transfusion. It is believed that the transfusion process was probably at fault. The blood was withdrawn about 4 cc at a time and the material was infused directly into the right heart through the jugular vein. The probable cause of death was a weakening of the heart as a result of the administration technique employed.

(d) A total of 6 cc of material (equivalent to about 4 units of blood in a human patient) was administered intravenously without withdrawal of blood. The animal was a long-term survivor.

EXAMPLE 8

The material employed was a 45% by volume suspension of cells (11.45 gm percent hemoglobin) in Krebs-Ringers solution (pH 7.4) with an antibiotic. The material was administered by a technique wherein an infusion pump was employed to effect simultaneous withdrawal of blood from the femoral artery and infusion of the material into the femoral vein. A total of 22 cc (approximately 150% of blood volume) was administered over a period of 55 minutes at which time the animal died, apparently of disseminated intravascular coagulation — probably the result of stromal lipid contamination of the hemoglobin.

EXAMPLE 9

The material administered consisted of a 7.5 gm percent hemoglobin in Krebs-Ringers solution to which 5% by weight albumin was added. Synthetic erythrocytes were prepared by the film method above described, using one part cholesterol, one part synthetic lecithin, and one part dicetyl phosphate as a substitute for phosphatidic acid. After sonication, the particles were filtered and those having a diameter in excess of about 0.8 microns were discarded. The hematocrit of the final solution was roughly 20. About 5 cc of the material (equivalent to 2½ units of blood in a human patient) was intravenously administered to a rat and the animal was a long-term survivor.

It will be understood that various modifications and variations may be expected without departing from the spirit or scope of the novel concepts of our invention.

What is claimed is:

1. A synthetic cell for use in oxygen and carbon dioxide transport as an in vivo substitute for naturally-ocurring erythrocytes, said cell comprising a synthetic cell membrane of lipid material having stromafree hemoglobin encapsulated therein.

2. The cell of claim 1 wherein said lipid material includes a sterol.

3. The cell of claim 1 wherein said lipid material includes a phospholipid.

4. The cell of claim 3 wherein said phospholipid is selected from the group consisting of lecithin, cephalin, sphingomyelin, phosphatidic acid, phosphatidyl serine, phosphatidyl inositol, phosphatidyl choline, phosphatidyl ethanolamine, and mixtures thereof.

5. The cell of claim 3 wherein said cell is substantially spherical and has a diameter of from about 0.1 to about 10 microns.

6. The cell of claim 1 wherein said lipid material includes, in combination, cholesterol, lecithin and phosphatidic acid in a ratio of approximately one part by weight cholesterol to two parts by weight of combined lecithin and phosphatidic acid.

7. The cell of claim 1 wherein said lipid material includes, in combination, cholesterol, lecithin and phosphatidic acid in a ratio of approximately one part by weight cholesterol to three parts by weight of combined lecithin and phosphatidic acid.

8. A composition comprising the cell of claim 1 in combination with a liquid carrier physiologically compatible with a host animal to whom the composition is administered.

9. The composition of claim 8 wherein said liquid carrier is selected from the group consisting of normal saline and Krebs-Ringers solutions.

10. The composition of claim 8 wherein said liquid carrier is a synthetic plasma selected from the group consisting of dextran, hydroxyethyl starch and albumin solutions.

* * * * *